(12) United States Patent
Jarvis et al.

(10) Patent No.: US 10,315,131 B2
(45) Date of Patent: *Jun. 11, 2019

(54) ISOLATION OF INTERFACIAL MATERIAL FROM ORGANIC MATRICES

(71) Applicant: Florida State University Research Foundation, Inc., Tallahassee, FL (US)

(72) Inventors: Jacqueline M. Jarvis, Tallahassee, FL (US); Ryan P. Rodgers, Tallahassee, FL (US); Winston K. Robbins, Brunswick, ME (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 614 days.

This patent is subject to a terminal disclaimer.

(21) Appl. No.: 14/060,268

(22) Filed: Oct. 22, 2013

(65) Prior Publication Data

US 2014/0110343 A1    Apr. 24, 2014

Related U.S. Application Data

(60) Provisional application No. 61/716,825, filed on Oct. 22, 2012.

(51) Int. Cl.
   *B01D 15/26* (2006.01)
   *B01J 20/10* (2006.01)
   (Continued)

(52) U.S. Cl.
   CPC ......... *B01D 15/265* (2013.01); *B01J 20/103* (2013.01); *B01J 20/28064* (2013.01);
   (Continued)

(58) Field of Classification Search
   None
   See application file for complete search history.

(56) References Cited

U.S. PATENT DOCUMENTS

2015/0225655 A1* 8/2015 Adams ................. C10G 33/04
                                                         516/138

FOREIGN PATENT DOCUMENTS

WO    WO 9931199 A1 *  6/1999  ............. C10G 25/00
WO       2014043404 A1     3/2014

OTHER PUBLICATIONS

Goual, Lamia. et al. Adsorption of Bituminous Components at Oil/Water Interfaces Investigated by Quartz Crystal Microbalance: Implications to the STability of Water-in-Oil Emulsions. Langmuir 2005, 21, 8278-8289.*

(Continued)

*Primary Examiner* — Kara M Peo
(74) *Attorney, Agent, or Firm* — Fox Rothschild LLP

(57) ABSTRACT

A method for preparing a crude oil solution for analysis, including adding water to a porous adsorbent to obtain a supported water substrate, having a plurality of water monolayers disposed on the porous adsorbent. The method further includes exposing the crude oil solution to the supported water substrate for a period of time; separating the supported water substrate from the crude oil solution; washing the supported water substrate with a water immiscible solvent to remove at least one hydrocarbon; displacing water from the plurality of water monolayers and the at least one interfacially active compound from the porous adsorbent with an alcohol and a co-solvent to obtain a displaced phase. The displaced phase can include the water, the at least one interfacially active compound, the alcohol, and the co-solvent. Finally, the method can include drying the displaced phase to isolate the at least one interfacially active compound.

5 Claims, 8 Drawing Sheets

(51) Int. Cl.
*G01N 33/28* (2006.01)
*B01J 20/28* (2006.01)
*B01D 15/08* (2006.01)
*B01J 20/02* (2006.01)
*B01D 39/20* (2006.01)
*B01D 39/06* (2006.01)
*B01D 39/02* (2006.01)
*B01D 39/00* (2006.01)
*G01N 30/00* (2006.01)
*G01N 13/02* (2006.01)
*C02F 1/28* (2006.01)
*C09K 3/32* (2006.01)
*C02F 1/42* (2006.01)

(52) U.S. Cl.
CPC ......... *G01N 33/2823* (2013.01); *B01D 15/08* (2013.01); *B01D 39/00* (2013.01); *B01D 39/02* (2013.01); *B01D 39/06* (2013.01); *B01D 39/2006* (2013.01); *B01J 20/02* (2013.01); *B01J 20/0251* (2013.01); *B01J 20/10* (2013.01); *B01J 20/28057* (2013.01); *C02F 1/28* (2013.01); *C02F 1/281* (2013.01); *C02F 1/42* (2013.01); *C09K 3/32* (2013.01); *G01N 33/2835* (2013.01); *G01N 2013/0233* (2013.01); *G01N 2013/0275* (2013.01); *G01N 2030/486* (2013.01)

(56) References Cited

OTHER PUBLICATIONS

Wu, "Investigating the stability mechanism of water-in-diluted bitumen emulsions through isolation and characterization of the stabilizing materials at the interface", Energy Fuels (2003) 17: 179-190.

Daaou, M. Bendedouch, D. Water pH and surfactant addition effects on teh stability of an Algerian crude oil emulsion. Journal of Saudi Chemical Society (2012) 16, 333-337. King Saud University.

Gu et al.: "Isolation and Characterization of Interfacial Materials in Bitumen Emulsions", Energy & Fuels 2006, 20, 673-681.

* cited by examiner

ISOLATION OF INTERFACIAL MATERIAL FROM ORGANIC MATRICES

CROSS-REFERENCES TO RELATED APPLICATIONS

This application claims benefit under 35 U.S.C. § 119(e) to U.S. Provisional Patent Application Ser. No. 61/716,825 filed on Oct. 22, 2012, titled Silica Gel Isolation of Interfacial Material From Organic Matrices, which is hereby incorporated by reference in its entirety.

STATEMENT REGARDING FEDERALLY SPONSORED RESEARCH

This invention was made with government support under #DMR0654118 awarded by the National Science Foundation. The government has certain rights in the invention.

BACKGROUND OF THE INVENTION

1. Field of the Invention

The invention relates generally to isolation of interfacial materials, and more specifically to isolation of interfacial materials from crude oil samples.

2. Description of the Related Art

Procedures for the isolation of one or more interfacial materials from petroleum crude oil samples are needed. Isolation of interfacial materials from crude oil would be valuable to the petroleum industry in order to identify compounds that interact with water and that exist at interfacial boundaries between water and crude oil. Knowledge of the compounds that comprise interfacial layers would help determine emulsion stability within a particular crude oil, which would be valuable for petroleum recovery and processing efforts.

BRIEF SUMMARY OF THE INVENTION

Various methods relate to a method for preparing a crude oil solution for analysis, including adding water to a porous adsorbent to obtain a supported water substrate, having a plurality of water monolayers disposed on the porous adsorbent. The method further includes exposing the crude oil solution to the supported water substrate for a period of time; separating the supported water substrate from the crude oil solution; washing the supported water substrate with a water immiscible solvent to remove at least one hydrocarbon; displacing water from the plurality of water monolayers and the at least one interfacially active compound from the porous adsorbent with an alcohol and a co-solvent to obtain a displaced phase. The displaced phase can include the water, the at least one interfacially active compound, the alcohol, and the co-solvent. Finally, the method can include drying the displaced phase to isolate the at least one interfacially active compound.

Other embodiments relate to a column for preparing a crude oil solution for analysis. The column can include a porous adsorbent, such as silica gel, and water, wherein the water is present in an amount of from 50 to 66% by weight based on the weight of a porous adsorbent. The water can be disposed on the porous adsorbent in a plurality of monolayers.

BRIEF DESCRIPTION OF THE DRAWINGS

These and other features, aspects, and advantages of the present invention will become better understood with reference to the following description and appended claims, and accompanying drawings where:

Figure 1:
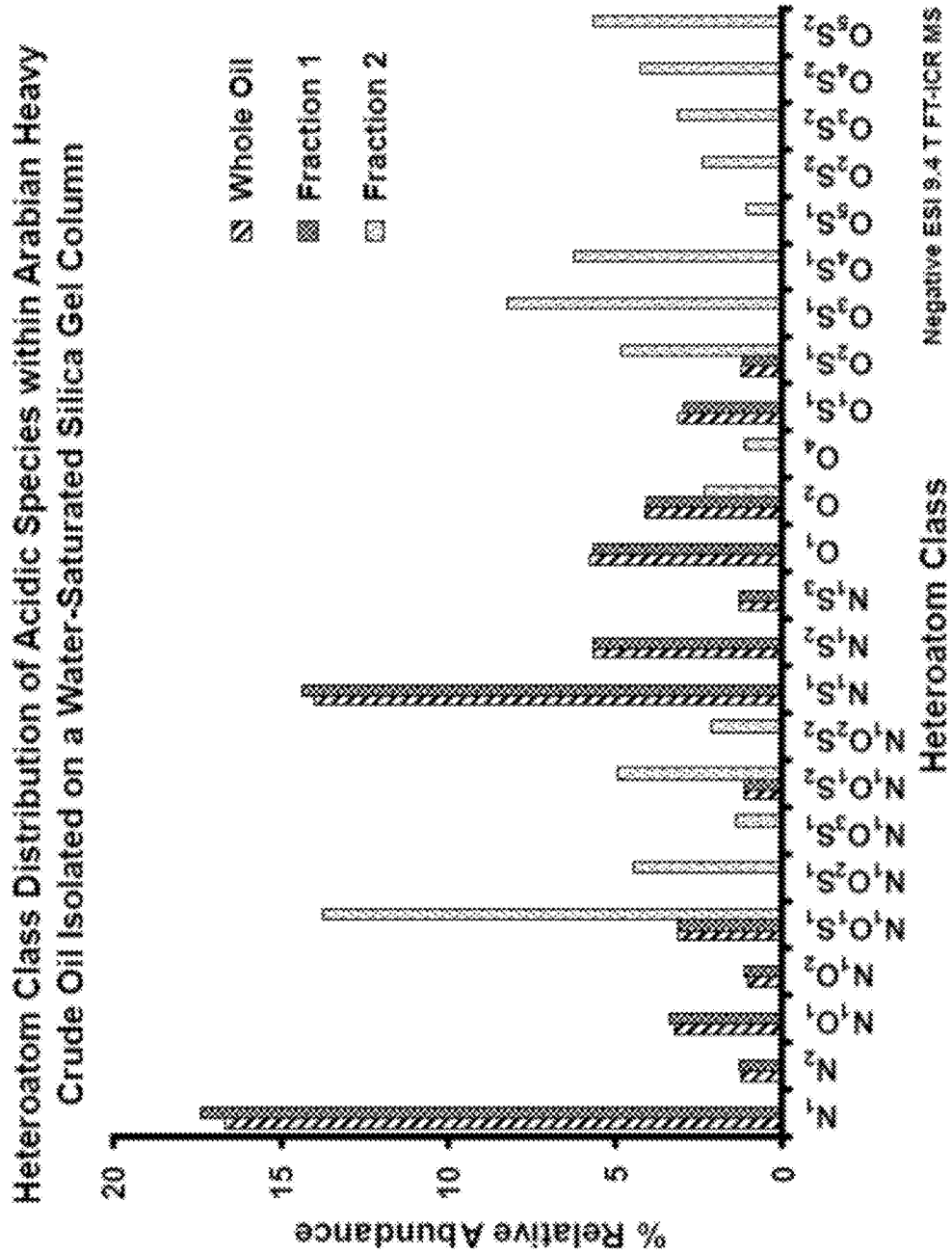
FIG. 1: shows heteroatom class distribution for the whole crude, fraction 1, and fraction 2 derived from (−) ESI 9.4 T FT-ICR. Mass spectra of Arab heavy crude oil.

It should be understood that the various embodiments are not limited to the arrangements and instrumentality shown in the drawings.

DETAILED DESCRIPTION OF THE INVENTION

The present invention may be understood more readily by reference to the following detailed description of preferred embodiments of the invention as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Various embodiments provide methods and procedures that can be used to isolate interfacial material from organic matrices. For purposes of the present invention, an "interfacial" or "interfacially active" material or compound refers to a compound that comprises an interface, lies at an oil/water interface and/or plays a role in emulsion stability, such as chemical species that accumulate at an interface, or in an ordered or structured manner due to the presence of an interface. These compounds are typically comprised of a nonpolar portion that interacts with the oil and a polar portion that interacts with water. Interfacially active materials are most typically found in the resin and asphaltene fractions of a crude oil. Of particular importance are procedures for the isolation of one or more interfacial materials from petroleum crude oil samples. Isolation of interfacial materials from crude oil is important to the petroleum industry in order to identify compounds that interact with water and that exist at interfacial boundaries between water and crude oil. Knowledge of the compounds that comprise interfacial layers can help determine emulsion stability within a particular crude oil, which is important for petroleum recovery and processing efforts.

According to one embodiment, a silica-gel supported water substrate can be prepared by combining silica gel with a predetermined weight of water for a predetermined time period at a predetermined temperature.

The predetermined weight of water can be within a range having a lower limit and/or an upper limit. The range can include or exclude the lower limit and/or the upper limit. The lower limit and/or upper limit can be selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, and 70 grams per 60 grams of silica gel. For example, according to certain preferred embodiments, the predetermined weight of water can be from 20 and 60 grams of water per 60 g dry silica gel, or preferably from 30-50 grams of water per 60 g dry silica gel, or more preferably 40 grams of water per 60 g dry silica gel.

The water can be present in an amount based on the weight of the porous adsorbent within a range having a lower limit and/or an upper limit. The range can include or exclude the lower limit and/or the upper limit. The lower limit and/or upper limit can be selected from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and 90% by weight. For example, according to certain preferred embodiments, the water can be present in an amount based on the weight of the porous adsorbent of from 50 to 66% by weight.

The predetermined time period can be within a range having a lower limit and/or an upper limit. The range can include or exclude the lower limit and/or the upper limit. The lower limit and/or upper limit can be selected from 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 15.25, 15.5, 15.75, 16, 16.25, 16.5, 16.75, 17, 17.25, 17.5, 17.75, 18, 18.25, 18.5, 18.75, 19, 19.25, 19.5, 19.75, 20, 20.25, 20.5, 20.75, 21, 21.25, 21.5, 21.75, 22, 22.25, 22.5, 22.75, 23, 23.25, 23.5, 23.75, and 24 hours. For example, according to certain preferred embodiments, the predetermined time period can be greater than 2 hours, overnight, or about 10 hours. Aging studies would require a longer time to allow the sample to interact with the stationary phase.

The predetermined temperature can be within a range having a lower limit and/or an upper limit. The range can include or exclude the lower limit and/or the upper limit. The lower limit and/or the upper limit can be selected from 0, 5, 10, 15, 20, 25, 30, 35, 40, 45, 50, 55, 60, 65, 70, 75, 80, 85, 90, 95, 100 degrees Celsius. For example, according to certain preferred embodiments, the predetermined temperature can be about 20-25 degrees Celsius.

When water is added to the silica gel, the water can adsorb into or onto the silica gel to form one or more monolayers equivalents. For purposes of the present invention, the term "monolayer equivalent" means the minimum number of water molecules required to completely cover a silica surface without any additional water molecules hydrogen bonded on top of this initial layer. Each additional layer of water molecules bound to the previous layer would comprise "1" monolayer. The number of monolayers equivalents of water formed on the silica gel can be within a range having a lower limit and/or an upper limit. The range can include or exclude the lower limit and/or the upper limit. The lower limit and/or upper limit can be selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 monolayer equivalents. For example, according to certain preferred embodiments, the number of monolayers of water formed on the silica gel can be from 20-30 monolayer equivalents.

The weight of water on the silica-gel supported water substrate can be dictated by the physical properties of the support, such as: surface area, pore volume, and pore size distribution.

Silica gels are produced by a variety of techniques that form small $SiO_2$—$Si(OH)_2$ beadlike primary particles which coalesce into interlocking strands that create a porous sorbent. The primary particles are in effect solid, sorbent porosity arises from the gaps between the strands. Many discussions of sorbent behavior assume cylindrical pores. The behavior of the irregular gaps in these sorbents are categorized by pore diameter as micropores, mesopores, or macropores. For purposes of the present invention the term "micropore" refers to a pore having a diameter of <20 Å; the term "mesopore" refers to a pore having a diameter of from 20-500 Å; and the term "macropore" refers to a pore having a diameter of from 500-4000 Å.

According to various embodiments, the pore size distributions of the porous adsorbents employed may be quite large. Typically, only mean pore diameter for a porous adsorbent, such as a silica gel adsorbent, is quoted while differences in the width of the distribution are ignored. Chromatographic silica gels are mostly mesoporous, because molecular diffusion into micropores is slow deteriorating column efficiency while macropores are formed at the expense of active surface area. For chromatography, pores should ideally have an open and regular shape to allow rapid mass transfer and consequently high column efficiency.

The overall specific surface area of sorbent includes their external and internal surface areas. The external surface area is typically rather small, but sometimes not negligible. Spherical particles of the porous adsorbent can have an external surface area within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, and 10 $m^2/g$. For example, according to certain preferred embodiments, spherical particles of the porous adsorbent can have an external surface area of about 0.5 $m^2/g$ for 5 g.

The internal surface area of sorbents can depend on their pore diameter and pore volume. Spherical particles of the porous adsorbent, having approximately 100 Å pores can have an internal surface area within a range having a lower limit and/or an upper limit. The range can include or exclude the lower limit and/or the upper limit. The lower limit and/or upper limit can be selected from 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, and 550 m$^2$/g. For example, according to certain preferred embodiments, spherical particles of the porous adsorbent, having approximately 100 Å pores can have an internal surface area of from 200 to 500 m$^2$/g. Spherical particles of the porous adsorbent, having approximately 1000 Å pores can have an internal surface area within a range having a lower limit and/or an upper limit. The range can include or exclude the lower limit and/or the upper limit. The lower limit and/or upper limit can be selected from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 m$^2$/g. For example, according to certain preferred embodiments, spherical particles of the porous adsorbent, having approximately 1000 Å pores can have an internal surface area of from 15 to 25 m$^2$/g. In other words, internal surface areas can vary from 200 to 500 m$^2$/g for silica gels with ~100 Å pores to 15 to 25 m$^2$/g those with ~1000 Å pores.

Again, the overall specific surface area of sorbent includes their external and internal surface areas. The porous adsorbent can have an overall specific surface area within a range having a lower limit and/or an upper limit. The range can include or exclude the lower limit and/or the upper limit. The lower limit and/or upper limit can be selected from 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, and 700 m$^2$/g. For example, according to certain preferred embodiments, the porous adsorbent can have an overall specific surface area of about 475 to 560 m$^2$/g.

Specific surface area is often estimated from by capillary nitrogen adsorption at 77 degrees K using B.E.T. calculations based on appropriate parameters. Nitrogen adsorption also yields the total pore volume available for liquid to condense within the capillaries of the sorbent. In B.E.T theory, liquids condense into capillaries filling the narrowest pores first. With "ink well" shaped peaks (such as the gaps between primary particles) filling would be expected to occur on the basis of the narrowest portion of the pore. Thus, adsorbents, such as mesoporous silica gel imbibe water until the exterior surface is nearly saturated with water. At this point the wet silica has a thin film of water on its exterior and at the mouth of each capillary. This available water surface area is much larger than just the exterior surface area of the silica gel particle because it has a nearly fractal contribution of the capillary catenary surface of each pore mouth.

When the surface of the silica is fully saturated with water, the pore mouths are completely full, reducing available water exposure to the particle exterior surface area. Furthermore, just beyond pore saturation, the silica is no longer free flowing and particles clump together, preventing its utility in adsorbing interfacial material.

The choice of sorbent properties will affect the quantities of water that are most effective for allowing the interfacial material to be isolated. For convenience, a chromatographic grade silica gel with a mean pore diameter of 60 Å has been used to illustrate isolation of interfacial material. Other mesoporous silica gels (or similar sorbents) are available with a range of surface areas and pore volumes that could be applied in this manner once optimized in water content. The porous adsorbent can have a mean pore diameter within a range having a lower limit and/or an upper limit. The range can include or exclude the lower limit and/or the upper limit. The lower limit and/or upper limit can be selected from 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, and 2000 Å. For example, according to certain preferred embodiments, the porous adsorbent can have a mean pore diameter of from 60 to 100 Å.

The minimum number of monolayers of water adsorbed onto the porous adsorbent, such as silica gel, can be identified as the number of monolayers where the supporting silica gel no longer influences the water interaction at the oil/water interface. The same physical properties dictate the upper weight of water added to support. According to various embodiments, the porous adsorbent can be silica gel, and the silica gel can have a surface area of about 500 m$^2$/g. At some point >100% the pores of the silica-gel supported water substrate are filled and the effective surface area is reduced to an unacceptable concentration. For example, when about 66% by weight of water is added to a typical silica gel (based on the total weight of the silica gel), <40% of the pores are filled and a substantial portion of the initial surface area is covered with ~26 monolayers of water. It should be noted, that adding more than about 20% by weight of water to the silica gel only serves to ensure that sufficient layers of water are present to allow the supported water to be independent of the support surface chemistry. While only the outermost layer or two of water may interact with the interfacially active compounds, it is possible that some of the materials found in samples will penetrate into the water layer.

Once the supported water substrate has been formed it may be exposed to crude oils, fractions or related compounds directly or in an appropriate solvent. Sample concentrations may vary from as little as 0.01% (vol:vol) sample in appropriate solvent to neat (undiluted) sample. This treatment can take many forms and is not limited to the following exemplary treatment techniques:

Batch Technique

According to certain exemplary embodiments, a portion of supported water substrate can be added to a sample solution comprising at least one interfacially active material. The sample solution can then be allowed to stand for a predetermined time period. The substrate can then be collected by filtration and washed with a non-polar solvent until the substrate is substantially free of a hydrocarbon phase. The interfacially active material can then be displaced from the substrate by washing the column with a mixed solvent containing alcohol and a co-solvent with good solvency properties for oils. The co-solvent can be, but is not limited to: aromatics, chlorinated solvents, ethers, esters, ketones, most specifically solvents such as toluene, dichloromethane, ethyl ether, ethyl acetate, or acetone. The displaced fluid can include both water, which may be desorbed from the silica gel, as well as the interfacially active compounds, and the mixed solvent. The displaced fluid may then be stripped to dryness. The interfacially active compounds can be dissolved in a solvent. The solvent can be selected from, but is not limited to, the co-solvents previously identified.

Packed Bed Technique

According to another exemplary embodiment, a sample solution, comprising at least one interfacially active compound and a solvent in which the compound is soluble, can be passed through a packed bed of the water supported substrate. This technique is preferable for many applications, because it combines the exposure and filtration steps described in the preceding batch technique.

According to either exemplary treatment technique, the sample (or sample solution) may be pre-equilibrated with water, if desired. The build-up of multiple layers of water on the silica-gel surface allows the one or more crude oil compounds to interact with the outermost layers of water while hindering direct interaction with the silica gel surface or pores. Retention of surface active, i.e., interfacially active, compounds from crude oil within the column is based upon the interaction of the compounds with water. Interfacially active materials are most typically polar species found in the resin and asphaltene fractions of a crude oil. These crude oil fractions can contribute individually and collectively to emulsion formation. Classes of compounds such sulfoxides, naphthenic acids, and N-heterocyclics and numerous other polar functionalities have been tested or suggested without conclusive evidence because of the lack of inadequate isolation procedures.

A variety of good petroleum solvents can be envisioned as diluents for testing emulsion effects of interfacially active species. These solvents are chosen to be immiscible with water and to mimic the base hydrocarbons in petroleum that constitute the bulk of the molecules in a crude sample. Low molecular weight (<150 amu) alkanes and aromatics typical of petroleum are used to reduce viscosity. Thus, solvents may include but are not limited to hexane, heptane, isooctane, toluene, xylenes, and methyl naphthalenes or mixtures thereof. The solvents or mixtures may be pre-equilibrated with water to minimize water stripping, although this is not routinely required. Solvent mixtures that more closely mimic crude oil composition are particularly effective. For example, various blends of heptane and toluene are often included, because the blend ratio can affect the incipient precipitation of asphaltenes. That is, pure heptane would not be practical, because some asphaltenes would fall out of solution before exposure; conversely, pure toluene is such a good solvent that some interfacially active compounds would not be collected at the solution/water interface. Typically, incipient precipitation occurs at heptane to toluene rations <50%. For illustration purposes, a water-unsaturated heptol with a 50:50 ratio of heptane to toluene has been employed. Heptol will remove any unretained crude oil compounds, or compounds that do not interact with the stationary phase (pass through the column and elute with the mobile phase), including, but not limited to: non-polar saturated hydrocarbons, aromatics, and non-polar NSO heterocyclics. Such unretained crude oil compounds can be completely soluble in Heptol.

According to various embodiments, incipient precipitation of unretained crude oil compounds such as asphaltenes in a crude oil sample can be induced using a solvent mixture comprising heptane and toluene in a predetermined ratio. The ratio of heptane to toluene in the solvent mixture can be selected from 100:0; 95:5; 90:10; 85:15; 80:20; 75:25; 70:30; 65:35; 60:40; 55:45; 50:50; 45:55; 40:60; 35:65; 30:70; 25:75; 20:80; 15:85; 10:90; 5:95; and 0:100. For example, according to certain preferred embodiments, the ratio of heptane to toluene in the solvent mixture can be 50:50.

The addition of any low molecular weight, water miscible alcohol, including but not limited to: methanol, ethanol, isopropyl alcohol, butanol, to the column can be sufficient to displace or to disrupt the outer water layers, stripping some of the water from the stationary phase, and allowing for the elution of the interfacial materials in combination with a supporting solvent, such as toluene, as discussed above. Toluene or alternative supporting solvents can be added with the alcohol for the second eluent to ensure the solubility of the compounds. Collection of the displacing solvent system can generate a fraction that contains both the water and the interfacially active compounds that were retained on the supported water of the stationary phase or interfacial material.

The displaced fraction can then be evaporated to dryness and dissolved in an appropriate supporting solvent to allow characterization of the isolated interfacially active material by various analytical techniques. Here, care should be taken to remove any fine residual silica particles that were displaced from the stationary phase during the elution of the interfacial material before any characterization is conducted. One way of reducing the interference of residual silica with analytical characterization is to transfer the interfacial material to a new vial in a compatible solvent (dichloromethane) that does not allow of the transfer of silica.

Ultimately, such analyses will reveal the elemental composition (class), the degree of unsaturation (aromaticity) and molecular composition of the interfacially active material. Studies of the isolated material can be used to rationalize differences among crude oils, devise control strategies for specific functionalities, or to identify contaminants that are contributing to emulsions. The supported water isolation technique can be used to track effects in laboratory emulsion studies. For example, isolation conditions can be adjusted to explore changes in the interfacially active material composition while ionic strength, cations, anions, or blending are varied in forming emulsions.

EXAMPLE

Techniques and Procedures 66.6% Water Saturated Silica Gel Preparation

Approximately 65 g of chromatographic silica gel (FisherScientific, 100-200 mesh, type 60A) was placed in a beaker and dried overnight in an oven at about 110° C. to remove any water from the silica gel. After drying, 40 g of HPLC water (JT Baker) was slowly added to 60 g of silica gel. The mixture was shaken in a capped vial until the silica gel and water mixed evenly. The silica gel appeared "dry" at the end and was free-flowing. Amounts can be changed to make as much or as little as needed; however, the proportion should be such to create 66.6% water on silica gel (based on the weight of silica gel).

63.9% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 3.9 g of HPLC water (JT Baker) was slowly added to 6.1 g of silica gel. The mixture was shaken in a capped vial until the silica gel and water mixed evenly. The silica gel appeared "dry" at the end and was free-flowing.

61.3% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 3.8 g of HPLC water (JT Baker) was slowly added to 6.2 g of silica gel. The mixture was shaken in a capped vial until the silica gel and water mixed evenly. The silica gel appeared "dry" at the end and was free-flowing.

58.7% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 3.7 g of HPLC water (JT Baker) was slowly added to 6.3 g of silica gel. The mixture was shaken in a capped vial until the silica gel and water mixed evenly. The silica gel appeared "dry" at the end and was free-flowing.

56.3% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 3.6 g of HPLC water (JT Baker) was slowly added to 6.4 g of silica gel. The mixture was shaken in a capped vial until the silica gel and water mixed evenly. The silica gel appeared "dry" at the end and was free-flowing.

53.8% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 3.5 g of HPLC water (JT Baker) was slowly added to 6.5 g of silica gel. The mixture was shaken in a capped vial until the silica gel and water mixed evenly. The silica gel appeared "dry" at the end and was free-flowing.

42.9% Water Saturated Silica Gel Preparation

Approximately 10 g of chromatographic silica gel (FisherScientific, 100-200 mesh, type 60A) was placed in a beaker and dried overnight in an oven at about 110° C. to remove any water from 7.0 g of silica gel. After drying, 3.0 g of HPLC water (JT Baker) was slowly added to the silica gel. The mixture was shaken in a capped vial until the silica gel and water mixed evenly. The silica gel appeared "dry" at the end and was free-flowing.

33.3% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 2.5 g of HPLC water (JT Baker) was slowly added to 7.5 g of silica gel. The mixture was shaken in a capped vial until the silica gel and water mixed evenly. The silica gel appeared "dry" at the end and was free-flowing.

25.0% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 2.0 g of HPLC water (JT Baker) was slowly added to 8.0 g of silica gel. The mixture was shaken in a capped vial until the silica gel and water mixed evenly. The silica gel appeared "dry" at the end and was free-flowing.

17.6% Water Saturated Silica Gel Preparation

Approximately 10 g of chromatographic silica gel (FisherScientific, 100-200 mesh, type 60A) was placed in a beaker and dried overnight in an oven at about 110° C. to remove any water from the silica gel. After drying, 1.5 g of HPLC water (JT Baker) was slowly added to 8.5 g of silica gel. The mixture was shaken in a capped vial until the silica gel and water mixed evenly. The silica gel appeared "dry" at the end and was free-flowing.

11.1% Water Saturated Silica Gel Preparation

Approximately 10 g of chromatographic silica gel (FisherScientific, 100-200 mesh, type 60A) was placed in a beaker and dried overnight in an oven at about 110° C. to remove any water from 9.0 g of silica gel. After drying, 1.0 g of HPLC water (JT Baker) was slowly added to the silica gel. The mixture was shaken in a capped vial until the silica gel and water mixed evenly. The silica gel appeared "dry" at the end and was free-flowing.

Sample Preparation 20 mL of heptol (50:50 heptane:toluene mixture, JT Baker, HPLC grade) was added to 1 g of crude oil (Arab Heavy) to create a 5% solution. 1 g of silica gel (66.6% water) was added to vial containing the 5% crude oil in heptol and the mixture was shaken by hand to generate a slurry.

5 mL of heptol (JT Baker, HPLC grade) was added to 250 mg of Athabasca Bitumen crude oil to create a 5% solution. 1 g of silica gel (11.1%-66.6% water) was added to the vial containing the 5% crude oil in heptol and the mixture was shaken by hand to generate a slurry.

Column Preparation/Loading

Glass wool was added to a 5 mL borosilicate glass pipet to create a barrier at the end of the pipet (column). The 5% crude oil in heptol/silica gel slurry was transferred to the column using a glass pipet. Additional heptol (up to about 5 mL) was used to rinse the sample vial, complete the transfer of the slurry, and ensure uniform column packing.

Interfacial Material Isolation 10 mL of heptol was passed through the column to remove any unretained compounds from the sample and the eluate was collected in a 40 mL glass vial (Fraction 1). 10 mL of a 10:25 part methanol:toluene solution was added to the column when the solvent level was about 5 mm from the top of the stationary phase. According to various embodiments, methanol can be replaced by another alcohol, such as ethanol. The eluate was collected in the first vial until the second eluate, which contains the interfacial material and appeared as light brown/cream-colored droplets, reached the end of the column. The second eluate was collected in a 25 mL glass vial (Fraction 2). Both vials were dried under $N_2$ gas until analytes were solvent-free. DCM was added to the vial that contained fraction 2 to allow for transfer of the interfacially active materials without transferring any silica that was also displaced in the second solvent system. The DCM solution was then transferred to a clean, preweighed vial prior to drying under $N_2$ gas to determine the final mass of material isolated.

Results and Discussion

The interfacial material from a heavy Arabian crude oil (Arab Heavy) was isolated on a 66.6% water saturated silica gel column. From about 1 g of crude oil, about 8 mg of interfacial material was isolated in the second fraction. FIG. 1 shows the first and second eluates as they came off the column (prior to drying). Fraction 1 corresponds to the unretained compounds from the crude oil and has the typical color of a heavy crude oil. Fraction 2 contains the compounds retained by the stationary phase, or interfacial material. The water stripped from the stationary phase can be seen at the bottom of fraction 2 as a cream-colored liquid. The organic layer of fraction 2 is significantly lighter than fraction 1.

FIG. 1 depicts the heteroatom class distribution (>1% relative abundance) for the whole Arab heavy crude, fraction 1, and fraction 2 derived from negative-ion electrospray 9.4 T Fourier transform ion cyclotron resonance mass spectrometry (ESI FT-ICR MS) broadband spectra. The whole crude and fraction 1 contain the same heteroatom classes in relatively the same abundances, dominated by nitrogen-containing classes, whereas fraction 2 contains different heteroatom classes, dominated by sulfur- and oxygen-containing classes. The results shown in FIG. 1 are summarized in Table 1.

TABLE 1

Relative Abundance of Heteroatom Classes Identified by FT-ICR MS within Arabian Heavy Crude Oil (1)

| Heteroatom Class | Relative % of Class within Whole Oil | Relative % of Class within Fraction 1 | Relative % of Class within Fraction 2 |
|---|---|---|---|
| $N_1$ | 16.68 | 17.38 | |
| $N_2$ | 1.23 | 1.27 | |
| $N_1O_1$ | 3.21 | 3.33 | |
| $N_1O_2$ | 1.02 | 1.12 | |
| $N_1O_1S_1$ | 3.08 | 3.07 | 13.76 |
| $N_1O_2S_1$ | | | 4.44 |
| $N_1O_3S_1$ | | | 1.34 |
| $N_1O_1S_2$ | 1.14 | 1.13 | 4.91 |
| $N_1O_2S_2$ | | | 2.12 |
| $N_1S_1$ | 14.01 | 14.38 | |
| $N_1S_2$ | 5.63 | 5.69 | |
| $N_1S_3$ | 1.26 | 1.27 | |
| $O_1$ | 5.78 | 5.69 | |
| $O_2$ | 4.07 | 4.04 | 2.31 |
| $O_4$ | | | 1.12 |
| $O_1S_1$ | 3.12 | 2.94 | |
| $O_2S_1$ | 1.18 | 1.18 | 4.83 |
| $O_3S_1$ | | | 8.23 |
| $O_4S_1$ | | | 6.25 |
| $O_5S_1$ | | | 1.06 |
| $O_2S_2$ | | | 2.36 |
| $O_3S_2$ | | | 3.06 |
| $O_4S_2$ | | | 4.25 |
| $O_5S_2$ | | | 5.66 |

Figure 2:
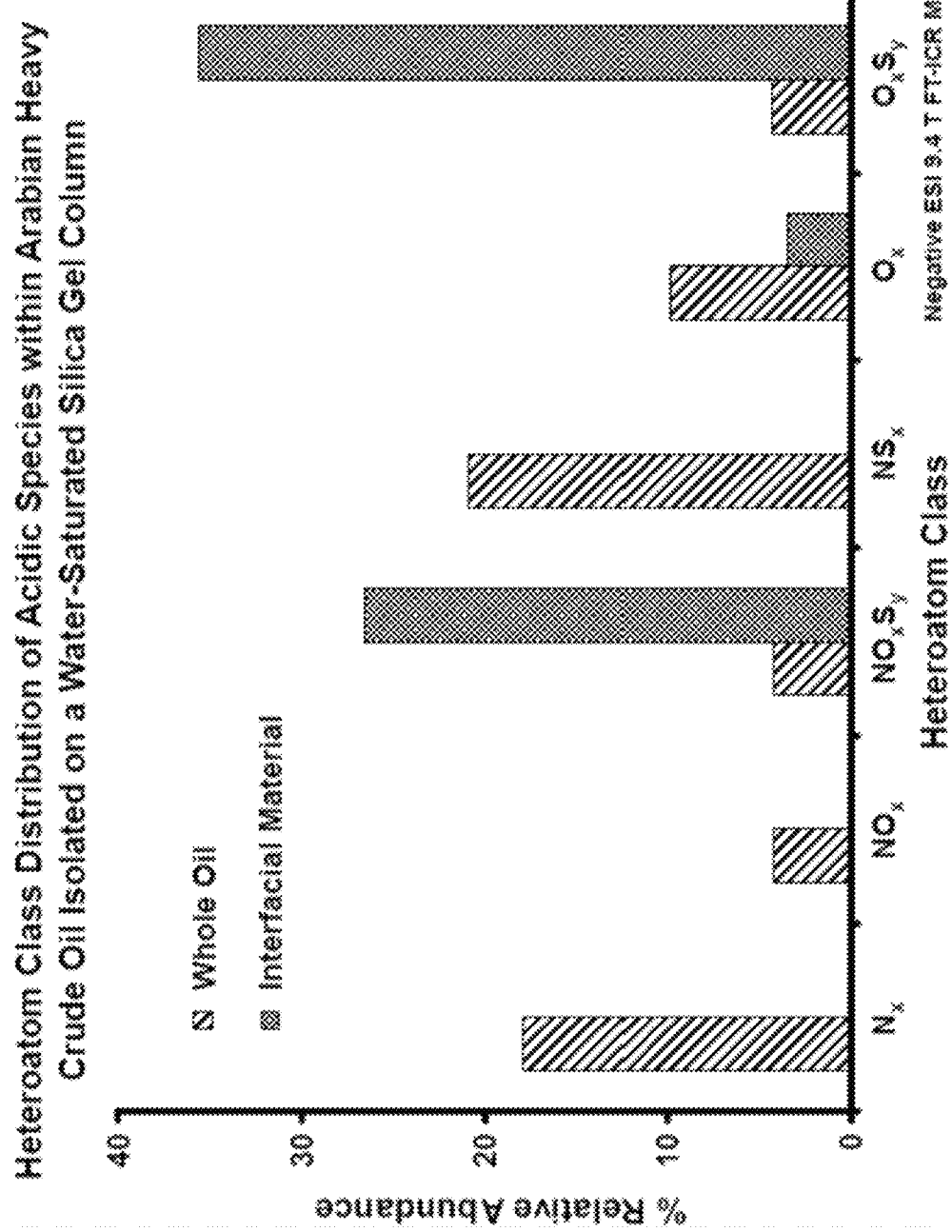
FIG. 2: shows heteroatom class distribution for the whole crude and interfacial material derived from (−) ESI 9.4 T FT-ICR mass spectra of Arab heavy crude oil.

FIG. 2 graphs the same heteroatom class information for the whole crude and fraction 2 (interfacial material). FIG. 2 shows heteroatom class distribution for the whole crude and interfacial material derived from (−) ESI 9.4 T FT-ICR mass spectra of Arab heavy crude oil. However, the similar heteroatom classes are combined for easier depiction of the differences between the whole crude and the interfacial material. The whole crude is characterized by $N_x$, $NS_x$, and $O_x$ species at ≥10% relative abundance (<10% relative abundance of $NO_x$, $NO_xS_y$, and $O_xS_y$ classes), whereas the interfacial material contains $O_xS_y$ and $NO_xS_y$ classes in >20% relative abundance (<5% relative abundance $O_x$). The results shown in FIG. 2 are summarized in Table 2.

TABLE 2

Relative Abundance of Heteroatom Classes Identified by FT-ICR MS within Arabian Heavy Crude Oil (2)

| Heteroatom Class | Relative % of Class within Whole Oil | Relative % of Class within Interfacial Material |
|---|---|---|
| $N_x$ | 17.91 | |
| $NO_x$ | 4.23 | |
| $NO_xS_y$ | 4.22 | |
| $NS_x$ | 20.90 | 26.57 |
| $O_x$ | 9.85 | 3.42 |
| $O_xS_y$ | 4.30 | 35.70 |

Figure 3:
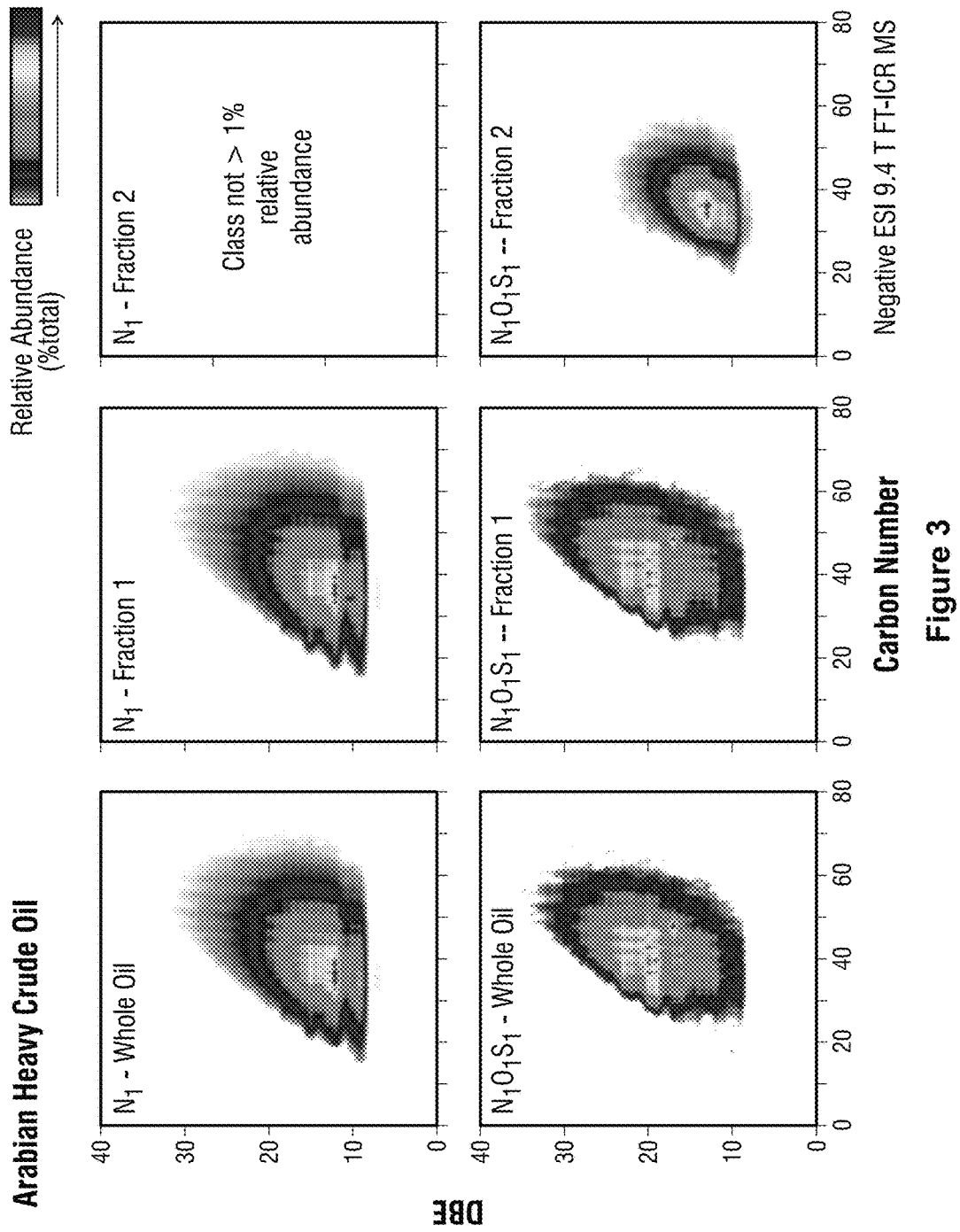
FIG. 3: shows negative-ion ESI 9.4 T FT-ICR MS isoabundance-contoured plots of double bond equivalents (DBE=rings+double bonds to carbon) vs. number of carbons for the $N_1$ and $N_1O_1S_1$ classes from the whole crude, fraction 1, and fraction 2 of Arab heavy crude oil.
Figure 4:
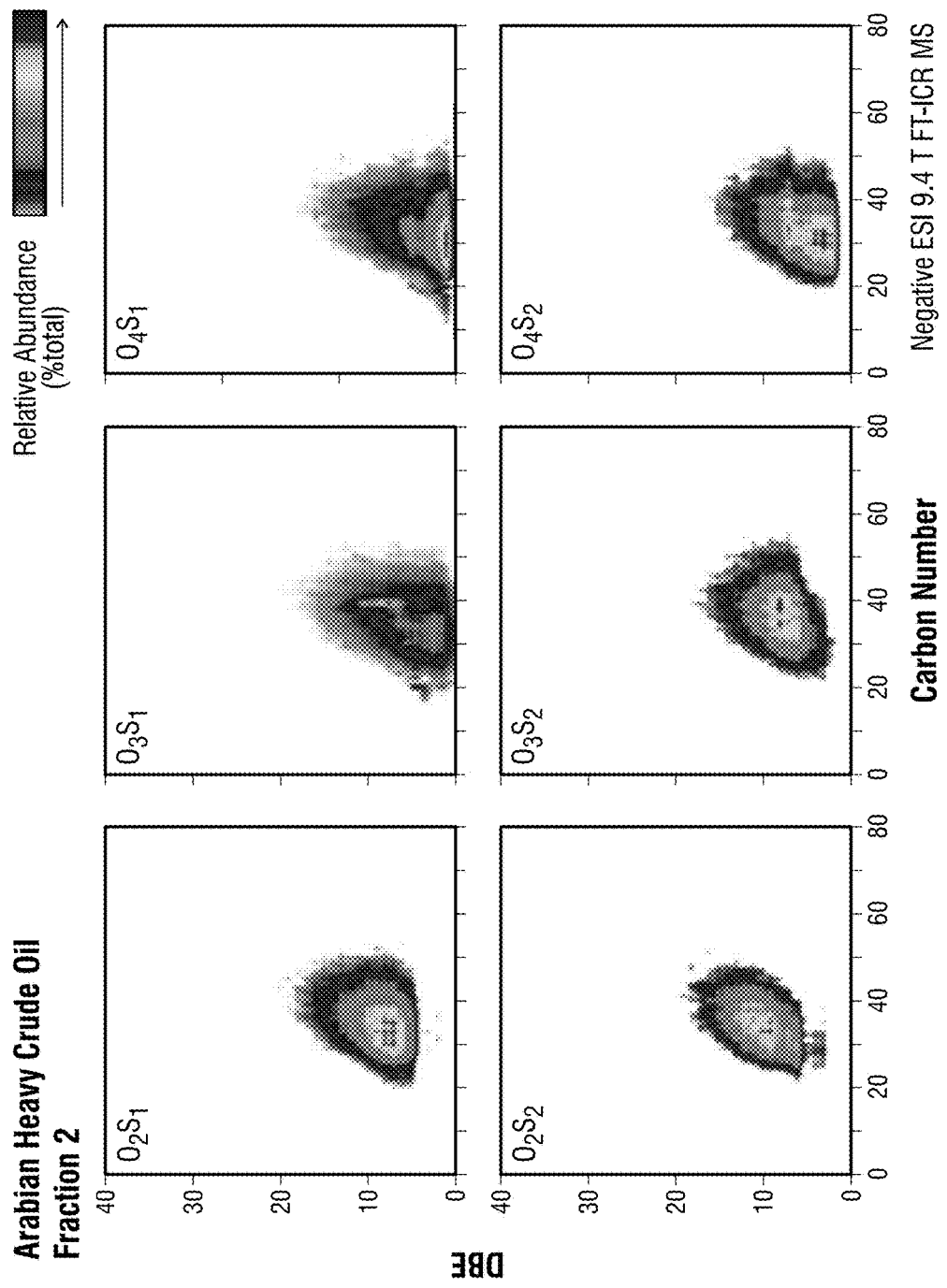
FIG. 4: shows negative-ion ESI 9.4 T FT-ICR MS isoabundance-contoured plots of DBE vs. number of carbons for various $O_xS_y$ classes from fraction 2 of Arab heavy crude oil.

From the isoabundance-contoured plots of the $N_1$ and $N_1O_1S_1$ classes from the whole crude, fraction 1, and fraction 2 (FIG. 3), it is apparent that the whole crude and fraction 1 cover the same compositional space, thus the two contain similar compounds, whereas fraction 2 covers different compositional space. The $N_1O_1S_1$ class of fraction 2 ranges in DBE from 9-25 whereas the compounds in the $N_1O_1S_1$ class of the whole crude and fraction 1 range from DBE 9-35. However, the whole crude and both fractions contain the similar carbon numbers (~20-65). The lower DBE range of fraction 2 exists throughout the $O_xS_y$ classes as well (highest DBE=20) (FIG. 4). Most of the compounds in fraction 2 are low carbon number (<60) and low DBE (<25).

FIG. 4 shows negative-ion ESI 9.4 T FT-ICR MS isoabundance-contoured plots of DBE vs. number of carbons for various $O_xS_y$ classes from fraction 2 of Arab heavy crude oil. The $O_xS_y$ classes are more abundant in interfacial material isolated from petroleum crude oil. Most of the compounds are present at low carbon number (<60) and low DBE (<20), which is compositional space typically covered by water-soluble organic species.

Figure 5:
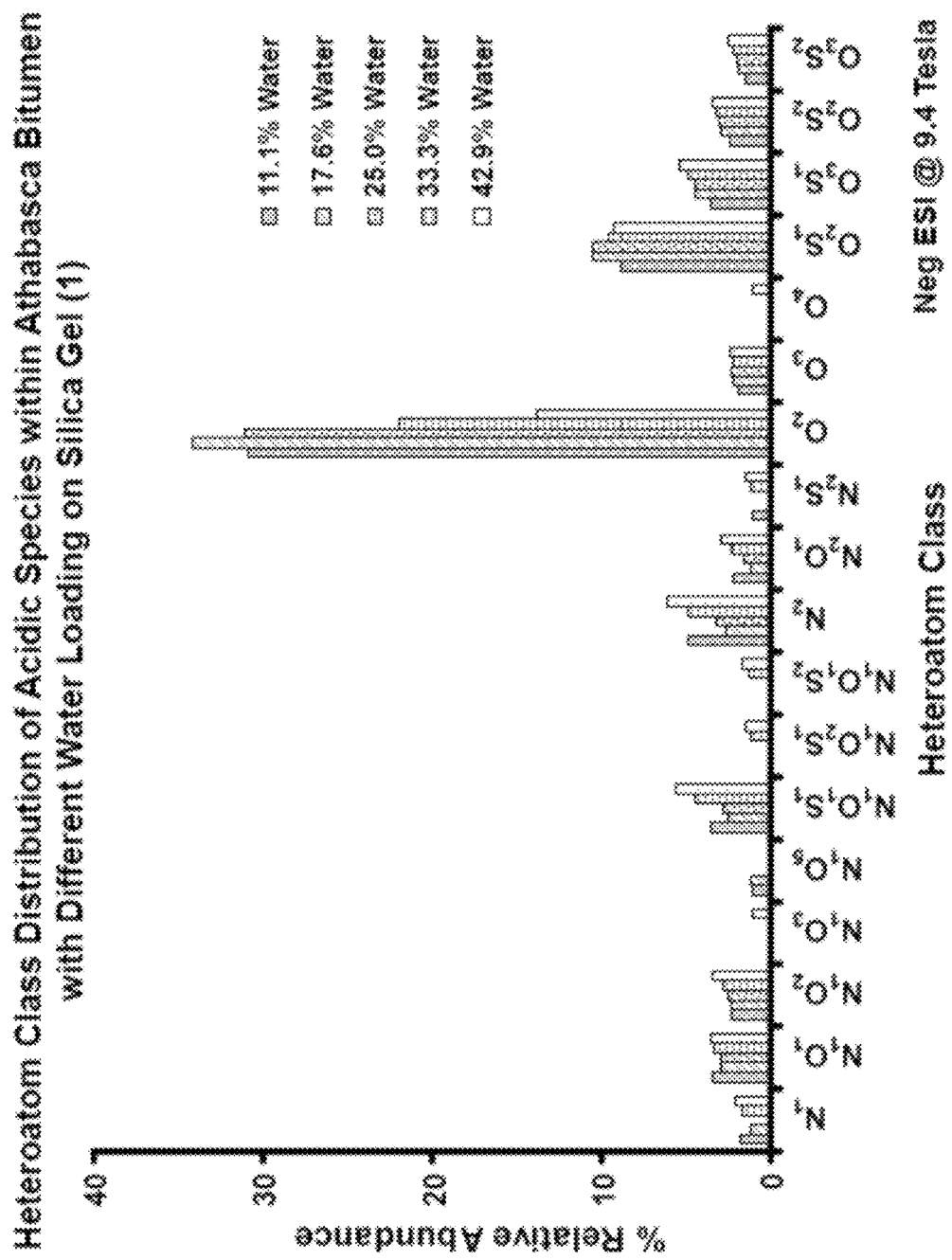
FIG. 5: shows heteroatom class distributions for fraction 2 collected with different water percentages (11.1%-42.9%) on silica gel derived from (−) ESI 9.4 T FT-ICR mass spectra of Athabasca bitumen.
Figure 6:
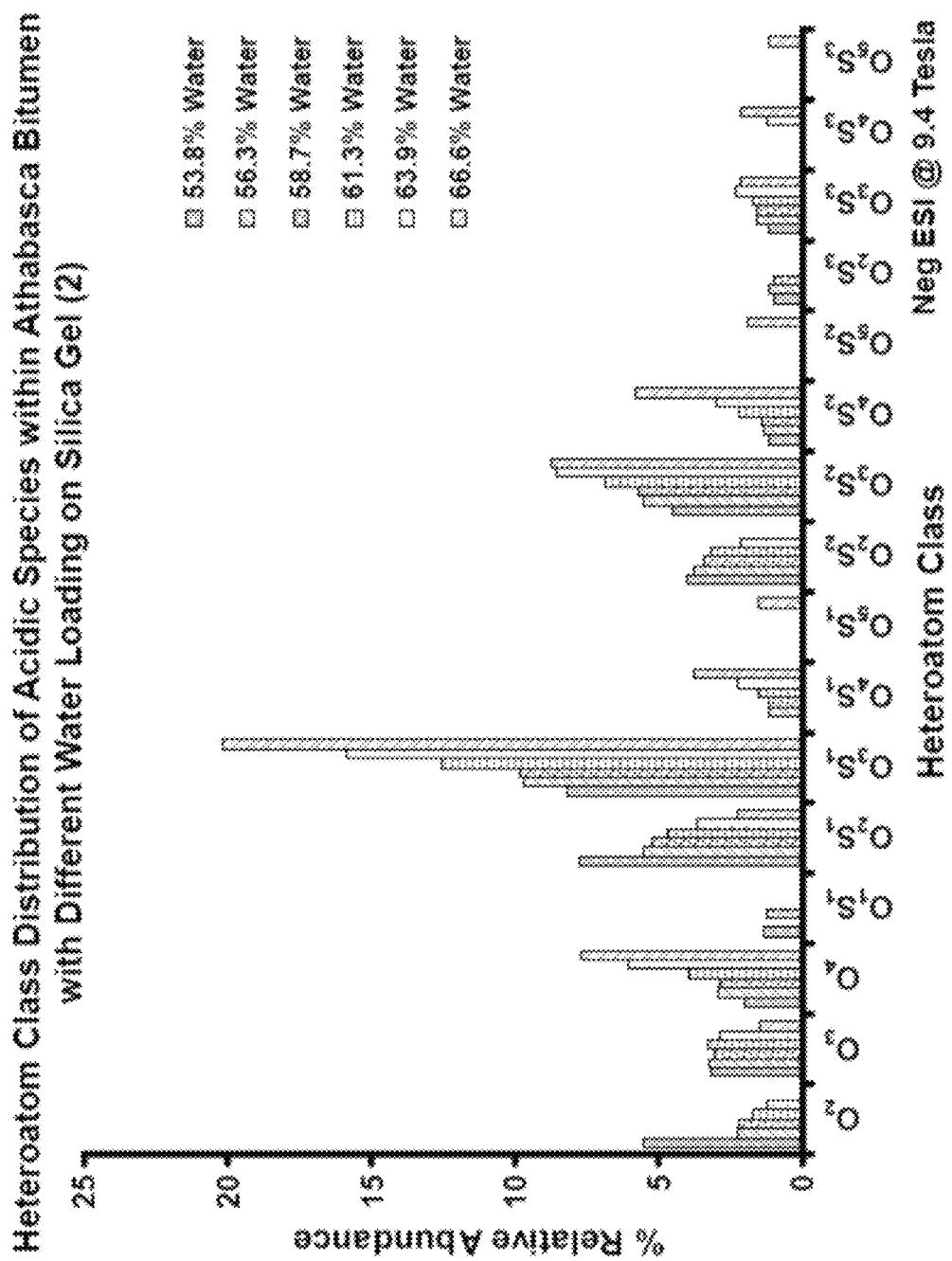
FIG. 6: shows heteroatom class distributions ($O_x$ and $O_xS_y$ species only) for fraction 2 collected with different water percentages (53.8%-66.6%) on silica gel derived from (−) ESI 9.4 T FT-ICR mass spectra of Athabasca bitumen.
Figure 7:
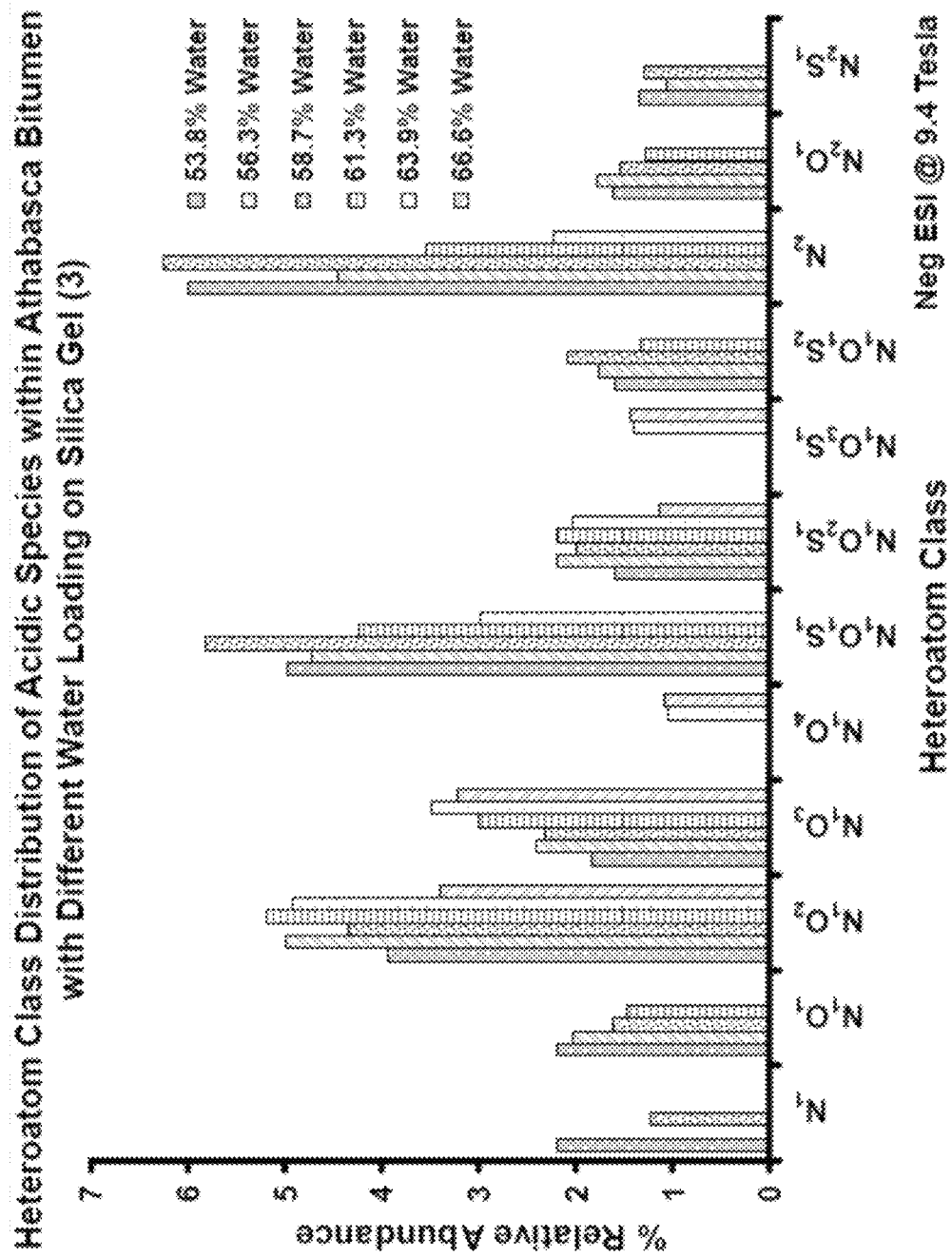
FIG. 7: shows heteroatom class distributions (nitrogen-containing species only) for fraction 2 collected with different water percentages (53.8%-66.6%) on silica gel derived from (−) ESI 9.4 T FT-ICR mass spectra of Athabasca bitumen.

FIGS. 5-7 show the selectivity of compounds isolated in fraction 2 of Athabasca bitumen by changing the percentage of water added to silica gel. FIG. 5 shows the heteroatom class distributions of species (>1% relative abundance) isolated in fraction 2 on 11.1-42.9% water on silica gel columns derived from (−) ESI FT-ICR mass spectra whereas FIG. 6 ($O_x$ and $O_xS_y$ species) and FIG. 7 (nitrogen-containing species) show the heteroatom class distributions of species isolated in fraction 2 on 53.8-66.6% water of silica gel columns. The major trends apparent are the decrease of $O_2$ species and increase in $O_3S_1$ species as the percentage of water on silica increases. Higher water percentages on silica gel (>60%) also show an increase in the retention of higher order $O_xS_y$ species. The increased number of water monolayers and/or coverage of pores affect the selectivity of the species retained on the stationary phase. The results shown in FIGS. 5-7 are summarized in Tables 3, 4, and 5.

TABLE 3

Relative Abundance of Heteroatom Classes Identified by FT-ICR MS within Athabasca Bitumen (1)

| Heteroatom Class | Relative % of Class Isolated 11.1% Water Column | Relative % of Class Isolated 17.6% Water Column | Relative % of Class Isolated 25.0% Water Column | Relative % of Class Isolated 33.3% Water Column | Relative % of Class Isolated 42.9% Water Column |
|---|---|---|---|---|---|
| $N_1$ | 1.83 | 1.20 | | 1.69 | 2.10 |
| $N_1O_1$ | 3.46 | 2.91 | 2.92 | 3.36 | 3.50 |

TABLE 3-continued

Relative Abundance of Heteroatom Classes Identified by FT-ICR MS within Athabasca Bitumen (1)

| Heteroatom Class | Relative % of Class Isolated 11.1% Water Column | Relative % of Class Isolated 17.6% Water Column | Relative % of Class Isolated 25.0% Water Column | Relative % of Class Isolated 33.3% Water Column | Relative % of Class Isolated 42.9% Water Column |
|---|---|---|---|---|---|
| $N_1O_2$ | 2.26 | 2.34 | 2.55 | 2.83 | 3.42 |
| $N_1O_3$ | | | | | 1.09 |
| $N_1O_5$ | 1.03 | 1.13 | | | |
| $N_1O_1S_1$ | 3.54 | 2.49 | 2.82 | 4.43 | 5.61 |
| $N_1O_2S_1$ | | | | 1.16 | 1.44 |
| $N_1O_1S_2$ | | | | 1.30 | 1.63 |
| $N_2$ | 4.84 | 2.61 | 3.24 | 4.83 | 6.09 |
| $N_2O_1$ | 2.21 | 1.17 | 1.54 | 2.27 | 2.88 |
| $N_2S_1$ | 1.11 | | | 1.20 | 1.50 |
| $O_2$ | 30.88 | 34.19 | 31.06 | 21.90 | 13.87 |
| $O_3$ | 1.93 | 2.22 | 2.31 | 2.22 | 2.38 |
| $O_4$ | | | | | 1.06 |
| $O_2S_1$ | 8.83 | 10.52 | 10.56 | 9.57 | 9.31 |
| $O_3S_1$ | 3.55 | 4.42 | 4.50 | 4.86 | 5.37 |
| $O_2S_2$ | 2.35 | 2.87 | 3.04 | 3.25 | 3.48 |
| $O_3S_2$ | 1.43 | 1.90 | 1.95 | 2.19 | 2.50 |

TABLE 4

Relative Abundance of Heteroatom Classes Identified by FT-ICR MS within Athabasca Bitumen (2)

| Heteroatom Class | Relative % of Class Isolated 53.8% Water Column | Relative % of Class Isolated 56.3% Water Column | Relative % of Class Isolated 58.7% Water Column | Relative % of Class Isolated 61.3% Water Column | Relative % of Class Isolated 63.9% Water Column | Relative % of Class Isolated 66.6% Water Column |
|---|---|---|---|---|---|---|
| $N_1$ | 2.20 | | 1.23 | | | |
| $N_1O_1$ | 2.19 | 2.04 | 1.62 | 1.47 | | |
| $N_1O_2$ | 3.93 | 5.00 | 4.35 | 5.19 | 4.93 | 3.40 |
| $N_1O_3$ | 1.83 | 2.40 | 2.33 | 2.99 | 3.49 | 3.22 |
| $N_1O_4$ | | | | | 1.04 | 1.08 |
| $N_1O_1S_1$ | 4.98 | 4.72 | 5.81 | 4.24 | 2.98 | |
| $N_1O_2S_1$ | 1.60 | 2.19 | 1.99 | 2.20 | 2.03 | 1.13 |
| $N_1O_3S_1$ | | | | | 1.40 | 1.43 |
| $N_1O_1S_2$ | 1.60 | 1.77 | 2.08 | 1.33 | | |
| $N_2$ | 5.99 | 4.45 | 6.25 | 3.54 | 2.22 | |
| $N_2O_1$ | 1.63 | 1.78 | 1.55 | 1.28 | | |
| $N_2S_1$ | 1.35 | 1.06 | 1.30 | | | |

TABLE 5

Relative Abundance of Heteroatom Classes Identified by FT-ICR MS within Athabasca Bitumen

| Heteroatom Class | Relative % of Class Isolated 53.8% Water Column | Relative % of Class Isolated 56.3% Water Column | Relative % of Class Isolated 58.7% Water Column | Relative % of Class Isolated 61.3% Water Column | Relative % of Class Isolated 63.9% Water Column | Relative % of Class Isolated 66.6% Water Column |
|---|---|---|---|---|---|---|
| $O_2$ | 5.52 | 2.27 | 2.18 | 1.72 | 1.24 | |
| $O_3$ | 3.14 | 3.20 | 3.06 | 3.31 | 2.84 | 1.45 |
| $O_4$ | 2.04 | 2.95 | 2.85 | 3.95 | 6.05 | 7.68 |
| $O_1S_1$ | 1.35 | | 1.20 | | | |
| $O_2S_1$ | 7.74 | 5.54 | 5.24 | 4.70 | 3.62 | 2.23 |
| $O_3S_1$ | 8.18 | 9.69 | 9.83 | 12.56 | 15.90 | 20.19 |
| $O_4S_1$ | | 1.18 | 1.16 | 1.56 | 2.24 | 3.78 |
| $O_5S_1$ | | | | | | 1.56 |
| $O_2S_2$ | 4.01 | 3.75 | 3.42 | 3.15 | 2.12 | |
| $O_3S_2$ | 4.47 | 5.53 | 5.73 | 6.87 | 8.52 | 8.72 |
| $O_4S_2$ | 1.17 | 1.38 | 1.39 | 2.22 | 2.99 | 5.83 |
| $O_5S_2$ | | | | | | 1.89 |
| $O_2S_3$ | 1.01 | 1.19 | 1.01 | | | |
| $O_3S_3$ | 1.16 | 1.62 | 1.58 | 1.70 | 2.30 | 2.12 |
| $O_4S_3$ | | | | | 1.22 | 2.14 |
| $O_5S_3$ | | | | | | 1.15 |

The amount of interfacial material isolated in fraction 2 is also dependent upon the percentage of water on the silica gel stationary phase. Table 5 shows the mass of fraction 2 recovered when about 250 mg of Athabasca bitumen was loaded unto silica gel containing different percentages of water (11.1-66.6%). The mass of material recovered in fraction 2 decreases with an increase in the percent of water on silica gel. Only the highest percentages of water (>60%) on silica gel showed no visible sign of interaction of compounds with the silica support.

TABLE 6

Mass Recovery of Fraction 2 with Different Water Loading on Silica Gel

| Water Percentage (%) on $SiO_2$ | Mass of Fraction 2 Recovered (mg) |
|---|---|
| 11.1 | 17.6 |
| 17.6 | 23.4 |
| 25.0 | 18.6 |
| 33.3 | 15.5 |
| 42.9 | 14.7 |
| 53.8 | 8.3 |
| 56.3 | 6.8 |
| 58.7 | 7.0 |
| 61.3 | 5.9 |
| 63.9 | 2.7 |
| 66.6 | 1.1 |

Figure 8:
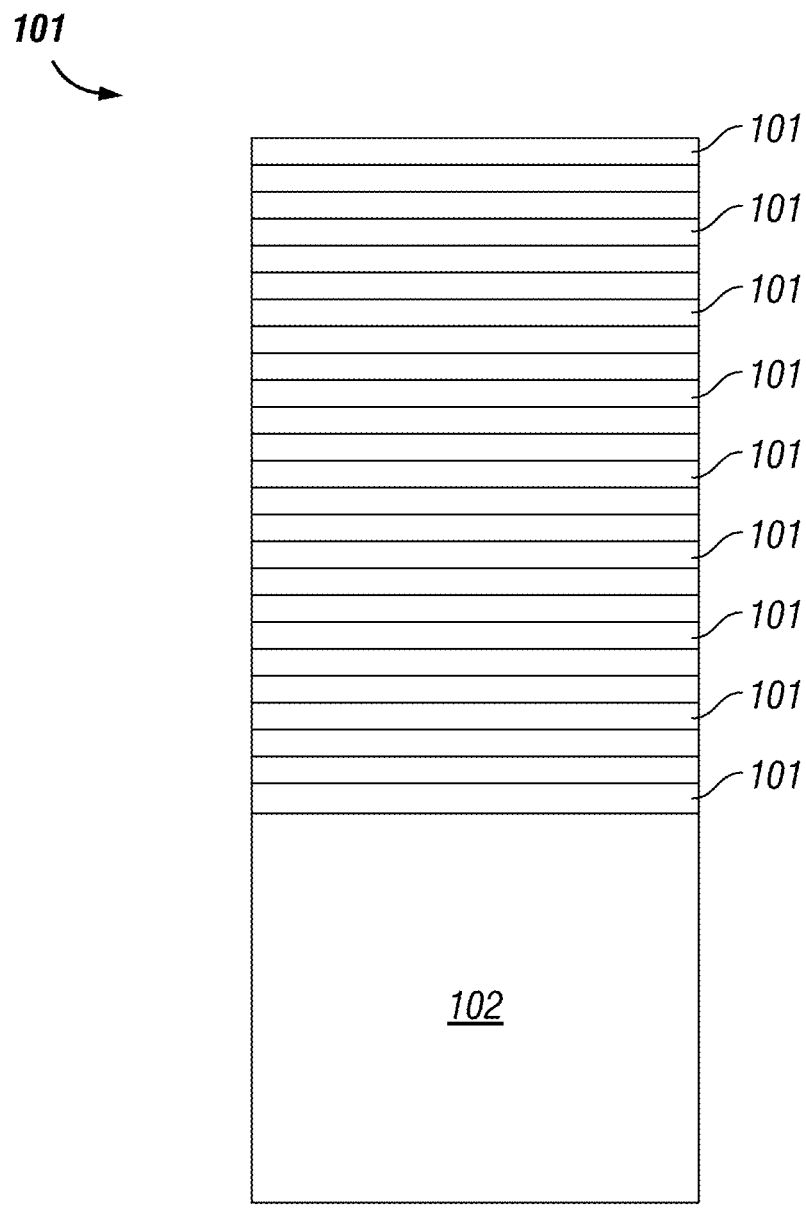
FIG. 8 is a schematic diagram of a supported water substrate according to various embodiments.

As shown in FIG. 8, a supported water substrate 101 can comprise a plurality of water monolayers 101 disposed on a porous adsorbent 102. Each of the plurality of water monolayers can have a thickness within a range having a lower limit and/or an upper limit. The range can include or exclude the lower limit and/or the upper limit. The lower limit and/or upper limit can be selected from 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 Å. For example, according to certain preferred embodiments, each of the plurality of water monolayers can have a thickness of from 2-3 Å.

The porous adsorbent 102 can have a thickness within a range having a lower limit and/or an upper limit. The range can include or exclude the lower limit and/or the upper limit. The lower limit and/or upper limit can be selected from 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, and 750 microns. For example, according to certain preferred embodiments, the porous adsorbent 102 can have a thickness of from 2-400 microns.

The porous adsorbent 102 can be in the form of a porous substrate. Alternatively, the porous adsorbent 102 can be in the form of a plurality of particles each having an average diameter within a range having a lower limit and/or an upper limit. The range can include or exclude the lower limit and/or the upper limit. The lower limit and/or upper limit can be selected from 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, and 750 microns. For example, according to certain preferred embodiments, the porous adsorbent 102 can be in the form of a plurality of particles each having an average diameter of 2-400 microns.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A method for analyzing a crude oil solution for the presence of at least one interfacially active compound in the crude oil solution, the method comprising:
    adding water to a porous adsorbent to obtain a supported water substrate, wherein the supported water substrate comprises from 10 to 30 water monolayers disposed on the porous adsorbent;
    exposing the crude oil solution to the supported water substrate for a period of time;
    separating the supported water substrate from the crude oil solution;
    washing the supported water substrate with a water immiscible solvent to remove at least one hydrocarbon while retaining the at least one interfacially active compound with the water monolayers on the supported water substrate;
    displacing water from the plurality of water monolayers and the at least one interfacially active compound from the porous adsorbent with an alcohol and a polar solvent for the interfacially active compound to obtain a displaced phase, wherein the displaced phase comprises the water, the at least one interfacially active compound, the alcohol, and the polar solvent; and
    drying the displaced phase to isolate the at least one interfacially active compound.

2. The method of claim 1, wherein the porous adsorbent is silica-gel.

3. The method of claim 1, wherein the porous adsorbent has a surface area of about 800 $m^2/g$.

4. The method of claim 1, wherein the period of time is greater than 2 hours.

5. The method according to claim 1, wherein the water immiscible solvent comprises about 50% by weight of heptane and about 50% by weight of toluene.

* * * * *